United States Patent [19]
Belden

[11] Patent Number: 5,824,032
[45] Date of Patent: Oct. 20, 1998

[54] MEDICAL ELECTRICAL LEAD FEATURING A ONE PIECE LEAD ANCHORING SLEEVE WITH WRAP-AROUND LOCKING ARMS

[75] Inventor: Elisabeth Lacy Belden, Plymouth, Minn.

[73] Assignee: Medtronic Inc., Minneapolis, Minn.

[21] Appl. No.: 694,976

[22] Filed: Aug. 9, 1996

[51] Int. Cl.$^6$ ................................................ A61N 1/05
[52] U.S. Cl. ........................ 607/126; 604/179; 607/116
[58] Field of Search ................................ 607/116, 122, 607/126, 130, 132; 604/174, 175, 178, 179, 283; 128/DIG. 26

[56] References Cited

U.S. PATENT DOCUMENTS

| | | | |
|---|---|---|---|
| 4,683,882 | 8/1987 | Laird | 604/179 X |
| 4,735,615 | 4/1988 | Uddo, Jr. et al. | 604/178 |
| 5,107,856 | 4/1992 | Kristiansen et al. | 607/132 X |
| 5,152,298 | 10/1992 | Kreyenhagen et al. | 607/116 |
| 5,242,431 | 9/1993 | Kristiansen | 604/283 |
| 5,250,033 | 10/1993 | Evans et al. | 604/160 |
| 5,273,053 | 12/1993 | Pohndorf | 607/132 |
| 5,395,343 | 3/1995 | Iscovich | 604/179 |
| 5,409,469 | 4/1995 | Schaerf | 604/282 |
| 5,441,504 | 8/1995 | Pohndorf et al. | 606/129 |
| 5,443,064 | 8/1995 | Theis et al. | 128/DIG. 26 X |

*Primary Examiner*—Jeffrey R. Jastrzab
*Attorney, Agent, or Firm*—Harold Patton; Michael J. Jaro

[57] ABSTRACT

A medical electrical lead featuring an improved anchoring sleeve. The improved anchoring sleeve includes a tubular sleeve having a central throughbore into which a medical electrical lead or catheter can extend. Integrally formed at one end of the anchoring sleeve is a securing portion having a partially annular portion with a slotted wall on one side, and a wrapping portion on the other side with a locking tabbed portion for securing to the slotted wall to grip the lead and secure it within the sleeve.

30 Claims, 5 Drawing Sheets

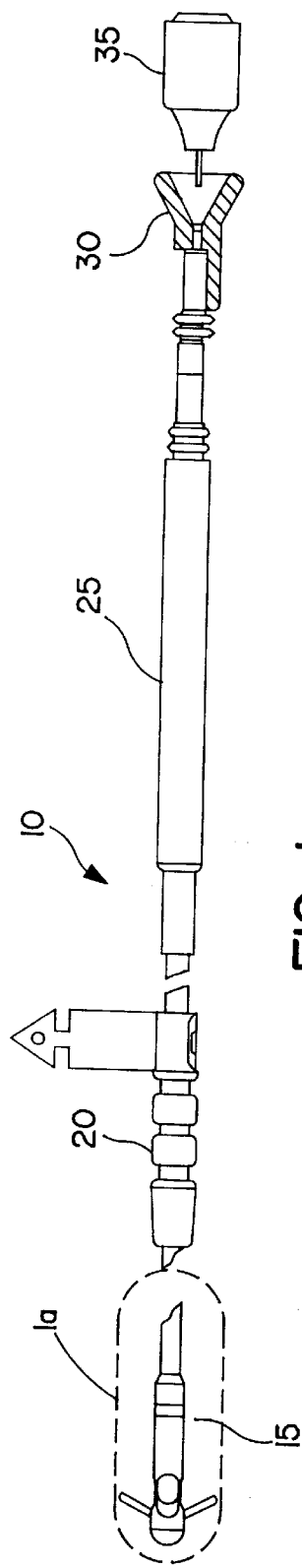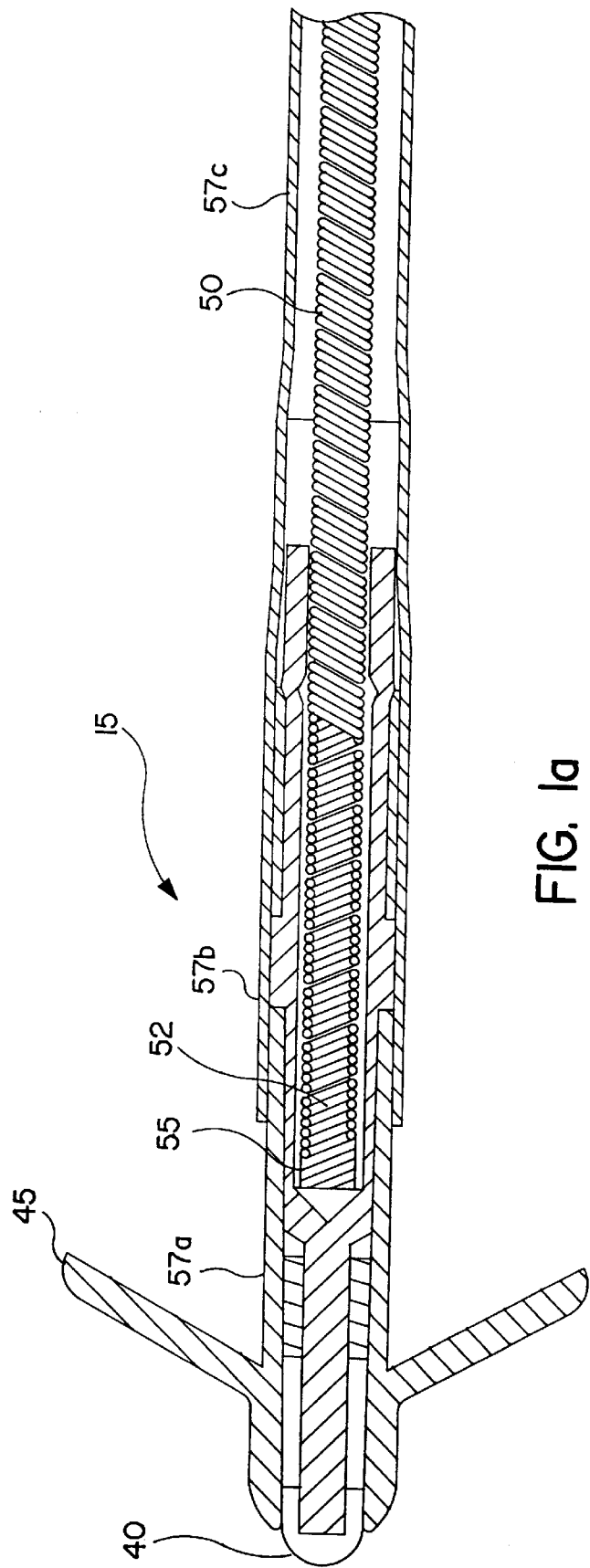

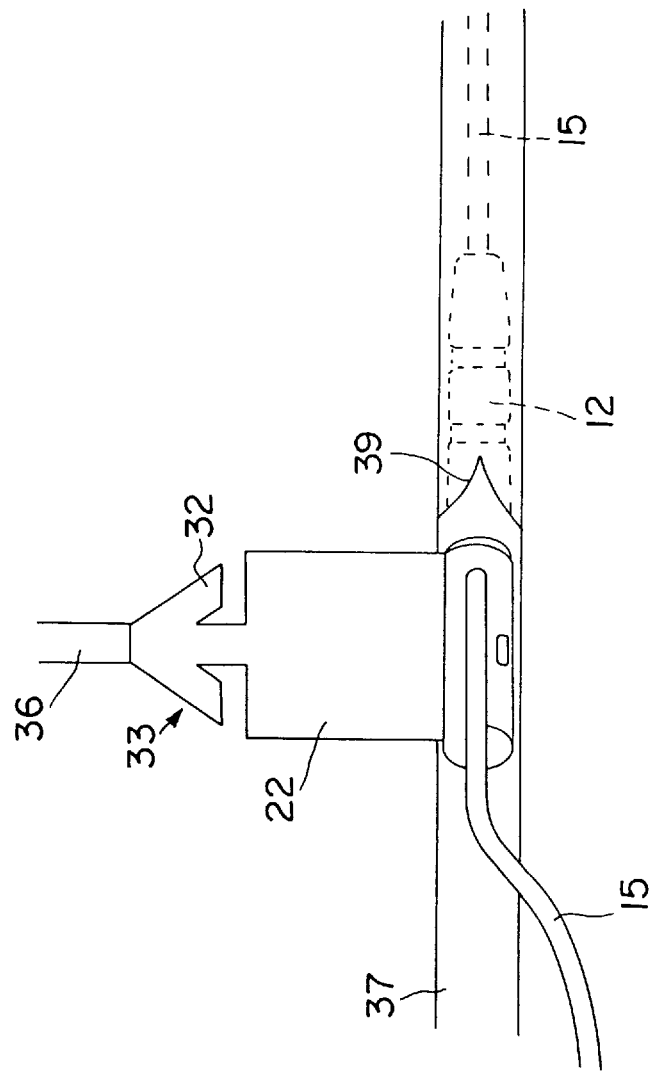

MEDICAL ELECTRICAL LEAD FEATURING A ONE PIECE LEAD ANCHORING SLEEVE WITH WRAP-AROUND LOCKING ARMS

BACKGROUND OF THE INVENTION

The present invention is directed toward the field of body implantable medical electrical leads, and in particular to an improved anchoring sleeve for securing a medical electrical lead to body tissue.

BACKGROUND ART

Endocardial leads are used in pacing systems to provide an electrical connection between a pacemaker and the heart. The pacemaker, connected to the proximal end of the medical electrical lead, transmits a signal through the lead to the lead's distal end to stimulate the endocardial tissue.

One method for introducing an endocardial lead into the heart is through a vein. It is important to properly anchor the lead body to tissue at the lead body's venous entry point. Improperly anchoring the lead body can cause the pacing system to malfunction, possibly causing harm to the patient.

Anchoring is generally accomplished by securing the lead body to an anchoring sleeve and, in turn, securing the anchoring sleeve to the body tissues. The lead body has typically been secured to the anchoring sleeve with sutures, namely by tightly tying sutures around suture grooves on the sleeve. The secured anchoring sleeve is then sutured to the tissue adjacent the lead's venous entry point to properly anchor the lead and prevent unwanted lead movement.

Existing anchoring sleeves have several drawbacks in their manner of attachment to the lead body. For example, a physician suturing the sleeve to the lead does not know how tight to tie the sutures securing the sleeve to the lead. The physician must rely on his experience securing these sleeves. A physician not familiar with the suture sleeve is more likely to tie the sleeve to the lead in an overly tight or too loose manner which can compromise the patient's health. Even after a physician becomes proficient at suturing a sleeve to a lead, the suturing process can lengthen the time of a procedure and may cause unwanted complications. Moreover, any physician may be faced with a distraction at the time he secures the sleeve to the lead, thus improperly securing it and subjecting the patient to potential harm.

The secured anchoring sleeve must be tight enough to prevent the lead body from sliding within the anchoring sleeve, but not so tight as to damage the lead body's insulation. Overly tight suturing could rupture the lead insulation and cause a short circuit or breakage of the lead. Physicians are often warned of the hazards associated with using such anchoring sleeves by the literature accompanying pacemaker products.

In view of these drawback, others have attempted to construct anchoring sleeves which did not require sutures to secure the anchoring sleeve to the lead body. For example, U.S. Pat. No. 5,242,431 by Kristiansen discloses an anchoring sleeve that does not require the use of sutures to compress the sleeve to the lead body. The sleeve of the '431 patent includes a tubular body with a first longitudinally extending portion, a second longitudinally extending portion, and a slidable collar which can be moved into a lead securing position. This sleeve, however, has several disadvantages, one being that its design calls for several parts, thereby complicating manufacturing and increasing costs. Another drawback is that this gripping mechanism is difficult to lock onto a lead body. The locking collar must be pushed or pulled into an interference fit on the sleeve. It is difficult for a physician to hold one part of the '431 sleeve in place while pulling or pushing the collar into a tight position over this other part of the sleeve.

Finally, the '431 sleeve has a high profile and is constructed of a rigid plastic. These features cause an increased tendency for the sleeve to wear through tissue over time. Also, such a bulky sleeve will form a subcutaneous protrusion that will be noticeable and irritating to the patient.

Because anchoring sleeves are implanted, it is desirous for anchoring sleeves to have a low profile, yet it is important that anchor sleeves do not fully enter the blood vessel they are associated with.

The present invention is directed toward overcoming one or more of the problems discussed above.

SUMMARY OF THE INVENTION

In one aspect of the invention, a lead anchoring sleeve has a tubular sleeve with a central lumen through which a medical electrical lead can extend. The sleeve has an integral flexible arm extending from the tubular sleeve, the arm having a partially annular portion with a slotted wall and a wrapping portion that lockably secures to the slotted wall.

It is an object of the invention to provide a reliable gripping mechanism for attaching an anchoring sleeve to a lead that provides a correct, simple and consistent gripping force each time it is used.

BRIEF DESCRIPTION OF THE DRAWINGS

FIG. 1 is a plan view of a medical electrical lead system featuring the anchoring sleeve of the present invention.

FIG. 1a is a cross-sectional view of a lead assembly portion of the lead system of FIG. 1.

FIG. 5 is a plan view showing the sleeve during the introduction of the lead into a vein.

Figure 2:
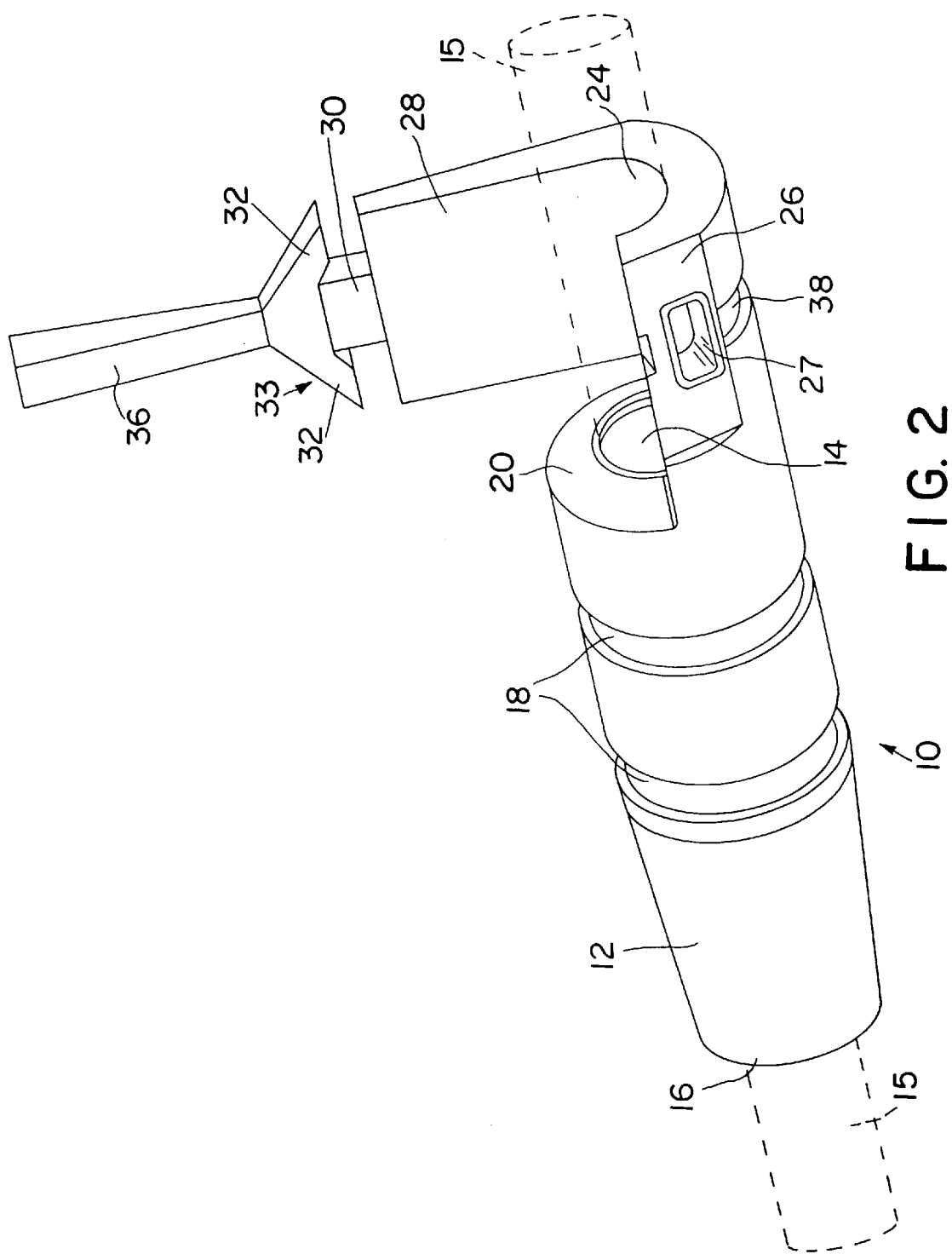
FIG. 2 is detailed perspective view of one preferred embodiment of the anchoring sleeve of the present invention in an unlocked position.

The FIGS. are not necessarily to scale.

DESCRIPTION OF THE PREFERRED EMBODIMENT

For the purposes of the specification and claims, the term "lead" is used herein in its broadest sense and includes pacing or defibrillation leads as well as any other types of stimulation leads, sensing leads, any combination thereof or any other elongated member, such as a catheter or tube, which may usefully be used within the body.

In a preferred embodiment of the present invention, a medical electrical lead comprises an electrode at a distal end thereof, a connector at a proximal end thereof and an elongated electrical conductor extending between the electrode and the connector, the conductor in electrical contact with the electrode at a distal end and in electrical contact with the connector at a proximal end, the conductor comprised of a plurality of wires or wire bundles wound in a multifilar coil configuration. Referring now to the drawings, FIG. 1 shows a lead system 10 which includes a lead assembly 15, an anchoring sleeve 20, a connector 25, a stylet guide 30, and a stiffening stylet 35. As is well known in the art, once implanted stylet guide 30, and a stiffening stylet 35 are removed from lead.

Referring now to FIG. 1a, the lead assembly 15 is shown in greater detail with an electrode structure 40 at a distal end of the lead assembly 15, a tine 45 to secure the lead assembly 15 to the endocardium, a lead conductor 50 in a multifilar coil configuration which allows the stiffening stylet 35 to be inserted into the lead assembly 15 in the internal lumen 52 of the lead conductor 50. The lead conductor 50 is shown attached at its distal end 55 to the electrode structure 40. The lead conductor 50 is also similarly attached at a proximal end (not shown) to the connector 25. In the preferred embodiment conductor 50 is a multifilar coil. Insulation elements 57a, 57b and 57c insulate portions of the electrode structure 40 and the lead conductor 50. Such insulation elements 57a, 57b, and 57c are preferably made from any suitable biocompatible polymer, such as silicone or polyurethane. The insulator 57c is typically a hollow polymeric tube extending between the proximal and distal ends of the lead assembly 15 and insulating the lead conductor 50 from surrounding body tissues. While a unipolar lead is shown, and described above, the present invention can also be applied to bipolar or tripolar leads in the same manner.

The preferred embodiment of the lead anchoring sleeve shown in FIG. 2 at 10 is made of silicone rubber. The anchoring sleeve 10 has a tube 12 with a throughbore or lumen 14 extending therethrough. The tube 12 has a tapered distal end 16 and at least one suture groove 18 for tying the sleeve to body tissue. The throughbore 14 is sized to receive a lead body 15 (shown in phantom in FIG. 2). The throughbore 14 has an interior diameter slightly greater than the lead body 15 exterior diameter. The lead body 15 is inserted in the throughbore 14, and the sleeve 10 is positioned upon the lead body 15. The tubular sleeve 10 has a discrete transition zone 20 with an interior diameter slightly less than the lead body 15 diameter, which provides a frictional fit to grip the lead body 15 and prevent the tubular sleeve 12 from sliding along the lead body under the force of gravity.

A flexible lead securing portion, or slotted wrapping arm, 22 has a partially annular portion 24 integral to and extending from a proximal end of the tubular sleeve 12. A slotted wall 26 having a thickness less than that of the partially annular portion 24 is formed along one edge of the partially annular portion 24. A flexible wrapping portion 28 of the lead securing portion 22 extends tangentially from the partially annular portion 24. This wrapping portion 28 decreases in thickness as it extends from the partially annular portion 24. The wrapping portion 28 also has a neck 30 extending from the edge furthest from the partially annular portion 24. This neck 30 connects a locking means 33 to the wrapping portion 28.

The securing portion, or wrapping arm, 22 has a suture groove 38 around which suture is wrapped when the anchoring sleeve is secured to the body tissue.

Figure 3:
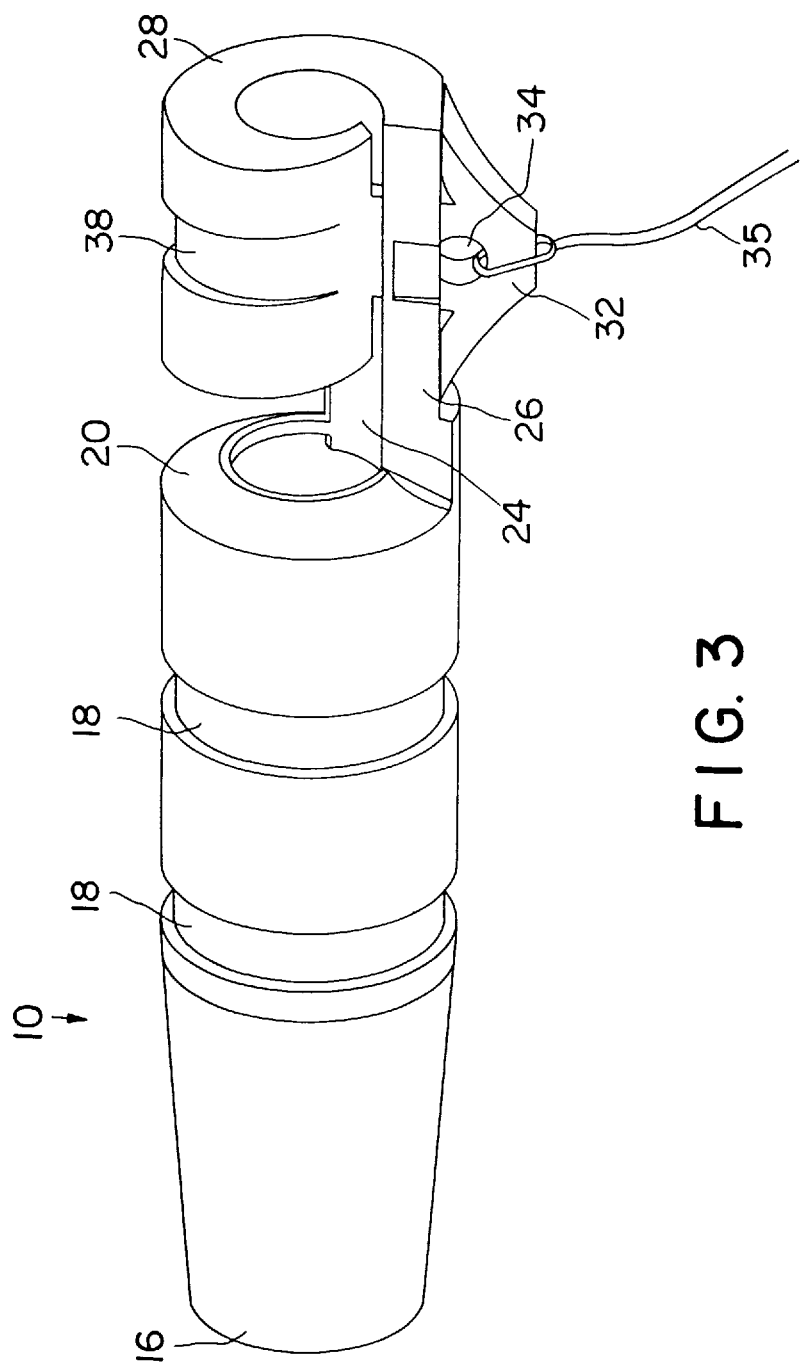
FIG. 3 is a perspective view of a second preferred embodiment of the anchoring sleeve of the present invention in a locked position.
Figure 4:
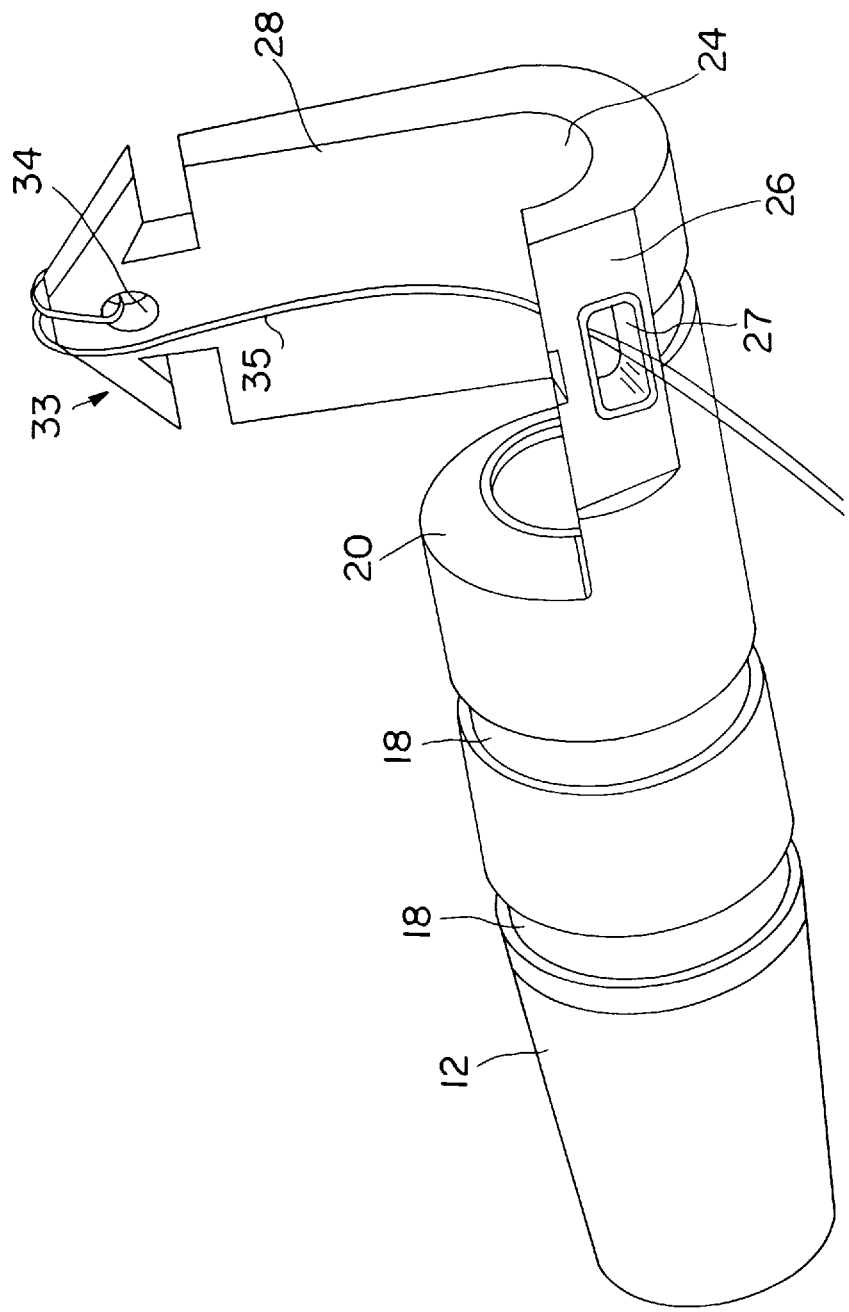
FIG. 4 is a perspective view similar to FIG. 2, showing the locking means guided by a suture ring.

The locking means 33 has a tabbed portion 32 that is lockably insertable to slot 27 on the slotted wall 26. The tabbed portion 32 has at least one pair of tabs extending from the neck 30. The locking means 33 further has an integral guiding means which guides the locking means 33 through the slot 27. The guiding means can be any number of structures; most preferably being a suture ring 34, as seen in FIG. 3 and FIG. 4, or a pull tab 36, as shown in FIG. 2, or both.

The suture ring 34 and slot 27 are preferably reinforced with a strong plastic material having radiopaque filler that acts as a location indicator. A suture 35 that extends through the slot 27 in the slotted wall 26 is tied to or looped around the suture ring 34, so that pulling this suture 35 through the slot 27 directs the locking tab 32 into a locked position. This suture 35 can then be threaded through a needle and used to secure the sleeve to body tissue.

The pull tab 36 (see FIG. 2) guides the locking means 33 into locked position when the pull tab 36 is directed through the slot 27. Pulling the pull tab 36 through the slot 27 sets the locking tabs 32 into locking position.

The neck 30 has a length that corresponds to the thickness of the slotted wall 26. The neck 30 is long enough to allow the locking tabs 32 to be disposed in locking position; but not so long as to allow enough slack in the wrapping portion 28 to release the sleeve's grip on the lead body 15. Because the neck 30 is made of silicone, when the locking means 33 is guided through the slot 27, the neck 30 stretches to a length greater than the thickness of the slotted wall 26 to allow the tabs 32 to be pulled through and clear the slot 27. Once the tabs 32 clear the slot 27, the pulling force can stop and the neck 30 returns to its original length for a snug fit.

When the locking means 33 are in locked position, the wrapping arm 22 holds the sleeve 10 on the lead body 15 with a minimum breakaway force of 0.25 lb. to prevent lead 15 dislodgment.

The operation of the preferred embodiment will now be described. When the physician is ready to anchor the lead to the venous entry point, the lead anchoring sleeve 10 is slid along the lead to its desired position. The sleeve's interior diameter allows clearance along the lead (except at the discrete transition zone, which offers frictional resistance) to allow the sleeve to be positionable on the body prior to suturing. The sleeve's tapered distal tip is positioned adjacent to the venous entry point 39 or within the vein at the entrypoint (in the case of a cephalic cut down) (see FIG. 5). The unfurled wrapping arm 22 is at the sleeve's proximal end, protruding to prevent the sleeve 10 from completely entering the vein 37. In order to secure the anchoring sleeve 10 to the desired location on the lead body 15 quickly and reliably, the physician guides the locking means 33 to the slot 27 and pulls the locking tabbed portion 32 through the slot 27 until locking occurs. Locking occurs when the tabs of the tabbed portion 32 have passed through the slot 27 and extend beyond slot 27 to prevent unintentional unlocking of the sleeve 10 about the lead body 15. The length of the wrapping arm 22 corresponds to the circumference of the lead body 15 so that the locked arm 22 has an interference fit on the lead body 15.

When the locking means 33 is secured in the slot 27 of the slotted wall 26, as seen in FIG. 3, the wrapping portion 28 of the wrapping arm 22 securely grips the lead body 15 with a consistent, predetermined pressure that prevents movement of the sleeve 10 along the lead body 15, yet does not damage the lead body.

Insertion of the locking means 33 through the slot 27 is preferably assisted by the guiding means. When the guiding means is the reinforced suture ring 34, the physician inserts the guiding suture 35 through the slot 27 and pulls the suture 35 until the tabbed portion 32 sets in locked position (see FIG. 3), causing the wrapping arm to securely hold the sleeve to the desired position on the lead body in a predetermined interference fit that will not damage the lead 15. This suture 35 is then attachable to a needle that pierces body tissue and guides the suture 35 under and around the lead to anchor the system to the tissue. During this anchoring, the suture is wrapped around the sleeve in suture grooves 18 and 38.

When the guiding means is a pull tab (see FIG. 2) the pull tab 36 is inserted and pulled through the slot 27 to a locked position wherein the tabbed portion 32 extends through the slot 27 and the wrapping portion 28 secures the lead body is with a predetermined safe and accurate interference fit.

Because the wrapping portion 28 has a tapered thickness (see FIG. 2), the locked and secured anchoring sleeve 10 has a low profile to prevent erosion through tissue and to decrease patient discomfort. Guiding means material that has passed through the slot 27 in locking the sleeve 10 can be cut off or flattened along the patient's chest to minimize obtrusiveness.

It will be seen from the foregoing that each of the embodiments of the wraparound anchoring sleeve provides a reliable and consistent means for the physician to secure the anchoring sleeve to the lead body. In addition to maintaining a low profile, these embodiments protect the lead insulation from suture stress, provide an ergonomically friendly means of locking the gripping arms and provide a marker to locate the lead body during future operations.

It is to be understood, that the present invention is not limited to use only in anchoring pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, the present invention may be employed in anchoring many of various types of therapeutic or diagnostic catheters and is not limited only to the introduction of electrical leads. For purposes of illustration only, however, the present invention is below described in the context of the introduction of endocardial pacing leads. For the purposes of this specification and claims, the term "lead" is used herein in its broadest sense and includes a stimulation lead, a sensing lead, a combination thereof or any other elongated member, such as a catheter or guide wire, which may usefully be introduced into the body.

Still other aspects, objects and advantages of the present invention can be obtained from a study of the specification, the drawings, and the appended claims. Furthermore, although the invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. A lead anchoring sleeve for anchoring medical leads and catheters to body tissue, the sleeve comprising:
   (a) a tubular sleeve having a central lumen through which a medical lead can extend;
   (b) a lead securing portion extending from the tubular sleeve, the securing portion having a partially annular portion generally aligned with the central lumen, a wall having a slot, and a wrapping portion, the wrapping portion having a locking means for securably connecting the wrapping portion to the wall having a slot.

2. The lead anchoring sleeve of claim 1 wherein the locking means comprise at least one locking tab.

3. The lead anchoring sleeve of claim 2 wherein the at least one locking tab is distanced from the wrapping portion by a neck.

4. The lead anchoring sleeve of claim 3 wherein the length of the neck is substantially equal to the thickness of the slotted wall.

5. The lead anchoring sleeve of claim 1 wherein the locking means further has, a guiding means to guide the locking means through the slotted wall.

6. The lead anchoring sleeve of claim 5 wherein the guiding means is a pull tab to guide the locking means through the slotted wall.

7. The lead anchoring sleeve of claim 1 wherein the locking means further has a pull tab to guide the locking means through the slotted wall.

8. The lead anchoring sleeve of claim I wherein the tubular sleeve has a tapered distal end.

9. The lead anchoring sleeve of claim 1 wherein the tubular sleeve has at least one circumferential suture groove.

10. The lead anchoring sleeve of claim 1 wherein the tubular sleeve has a transition zone at a proximal end of the tubular sleeve, the transition zone having an interior diameter less than the rest of the tubular sleeve.

11. The lead anchoring sleeve of claim 1 wherein the wrapping portion of the locking means decreases in thickness as the distance from the annular portion increases.

12. A lead anchoring sleeve for use in anchoring a medical electrical lead comprising:
    (a) a tubular sleeve with a central throughbore, the tubular sleeve having a lead extending through the throughbore;
    (b) a lead securing portion integral to the tubular sleeve, the securing portion having a partially annular portion integrally extending from an end of the tubular sleeve with a slot on one side and a flexible wrapping portion on the other side, and a tabbed locking portion on the flexible portion, whereby the tabbed locking portion is secured in a slot to frictionally secure the annular portion and wrapping portion around the lead.

13. The lead anchoring sleeve of claim 12 further comprising a transition zone between the sleeve and the securing portion, the transition zone having an interior diameter less than the interior diameter of the tubular sleeve.

14. The lead anchoring sleeve of claim 12 wherein the tabbed locking portion includes a reinforced ring securable to a suture for guiding the tabbed locking portion through the slot.

15. The lead anchoring sleeve of claim 12 wherein the tabbed locking portion includes a pull tab to guide the tab locking portion through the slot.

16. The lead anchoring sleeve of claim 15 wherein the tabbed locking portion includes a reinforced hole securable to a suture for guiding the tab locking portion into the slot.

17. The lead anchoring sleeve of claim 12 wherein the tabbed locking portion is distanced from the flexible portion by a neck portion.

18. The lead anchoring sleeve of claim 12 wherein the length of the neck is substantially equal to the thickness of the slot.

19. The lead anchoring sleeve of claim 12 wherein the flexible wrapping portion decreases in thickness as the distance from the partially annular portion increases.

20. A medical lead comprising:
    a lead body, the lead body having a conductor, an insulative sleeve positioned over a first coiled conductor;
    a terminal assembly positioned on a distal end of the lead body, the terminal assembly coupled to the conductor;
    an electrode positioned on the distal end of the lead body, the electrode coupled to the conductor; and an anchoring sleeve for anchoring the lead, the sleeve comprising a tubular sleeve having a central lumen through which the lead body extends, and a lead securing portion extending from the tubular sleeve, the securing portion having a partially annular portion generally aligned with the central lumen, a wall having a slot, and a wrapping portion, the wrapping portion having a locking means for securably connecting to the slotted wall.

21. The medical electrical lead of claim 20 wherein the locking means comprise at least one locking tab.

22. The medical electrical lead of claim 21 wherein the at least one locking tab is distanced from the wrapping portion by a neck.

23. The medical electrical lead of claim 22 wherein the length of the neck is substantially equal to the thickness of the slotted wall.

24. The medical electrical lead of claim 20 wherein the locking means further has a guiding means to guide the locking means through the slotted wall.

25. The medical electrical lead of claim 24 wherein the guiding means is a pull tab to guide the locking means through the slotted wall.

26. The medical electrical lead of claim 20 wherein the locking means further has a pull tab to guide the locking means through the slotted wall.

27. The medical electrical lead of claim 20 wherein the tubular sleeve has a tapered distal end.

28. The medical electrical lead of claim 20 wherein the tubular sleeve has at least one circumferential suture groove.

29. The medical electrical lead of claim 20 wherein the tubular sleeve has a transition zone at a proximal end of the tubular sleeve, the transition zone having an interior diameter less than the rest of the tubular sleeve.

30. The medical electrical lead of claim 20 wherein the wrapping portion of the locking means decreases in thickness as the distance from the annular portion increases.

* * * * *